(12) United States Patent
Koski

(10) Patent No.: US 12,383,489 B2
(45) Date of Patent: Aug. 12, 2025

(54) METHOD FOR PROVIDING A BEVERAGE ADDITIVE

(71) Applicant: ProBiora Health, LLC, Dallas, TX (US)

(72) Inventor: Christine Koski, Dallas, TX (US)

(73) Assignee: ProBiora Health, LLC, Jackson, WY (US)

( * ) Notice: Subject to any disclaimer, the term of this patent is extended or adjusted under 35 U.S.C. 154(b) by 402 days.

(21) Appl. No.: 18/098,033

(22) Filed: Jan. 17, 2023

(65) Prior Publication Data
US 2023/0218503 A1 Jul. 13, 2023

Related U.S. Application Data

(62) Division of application No. 16/036,789, filed on Jul. 16, 2018, now Pat. No. 11,559,479.

(51) Int. Cl.
| | |
|---|---|
| *A61K 8/99* | (2017.01) |
| *A23L 2/52* | (2006.01) |
| *A23L 33/135* | (2016.01) |
| *A61K 8/04* | (2006.01) |
| *A61Q 11/00* | (2006.01) |

(52) U.S. Cl.
CPC ........ *A61K 8/99* (2013.01); *A23L 2/52* (2013.01); *A23L 33/135* (2016.08); *A61K 8/044* (2013.01); *A61Q 11/00* (2013.01); *A23V 2002/00* (2013.01); *A23V 2400/237* (2023.08); *A61K 2800/5922* (2013.01); *A61K 2800/87* (2013.01); *A61K 2800/92* (2013.01)

(58) Field of Classification Search
CPC ................................. A61Q 11/00; A61K 8/99
USPC ..................................... 426/112, 115; 424/49
See application file for complete search history.

(56) References Cited

U.S. PATENT DOCUMENTS

| | | | |
|---|---|---|---|
| 5,170,888 | A | 12/1992 | Goncalves |
| 5,895,648 | A | 4/1999 | Cavaliere Vesely et al. |
| 6,105,760 | A | 8/2000 | Mollstam et al. |
| 2007/0098847 | A1 | 5/2007 | Teissier |

FOREIGN PATENT DOCUMENTS

| | | | | |
|---|---|---|---|---|
| AU | 2008317000 A1 | | 4/2009 | |
| CA | 2646511 A1 | * | 5/2008 | ............ A61J 7/0053 |
| EP | 1020123 A1 | | 7/2000 | |
| EP | 2341008 A2 | | 7/2011 | |

\* cited by examiner

*Primary Examiner* — Walter E Webb
(74) *Attorney, Agent, or Firm* — Fish IP Law, LLP

(57) ABSTRACT

Methods are described that provide controlled release of beneficial bacteria to the oral cavity. Such bacteria can subsequently colonize the oral cavity and displace or suppress the growth of pathogenic microorganisms. Described devices include a stabilized preparation of such beneficial bacteria and provide a consumable liquid, wet foam, or gel that includes such bacteria when used.

5 Claims, 2 Drawing Sheets

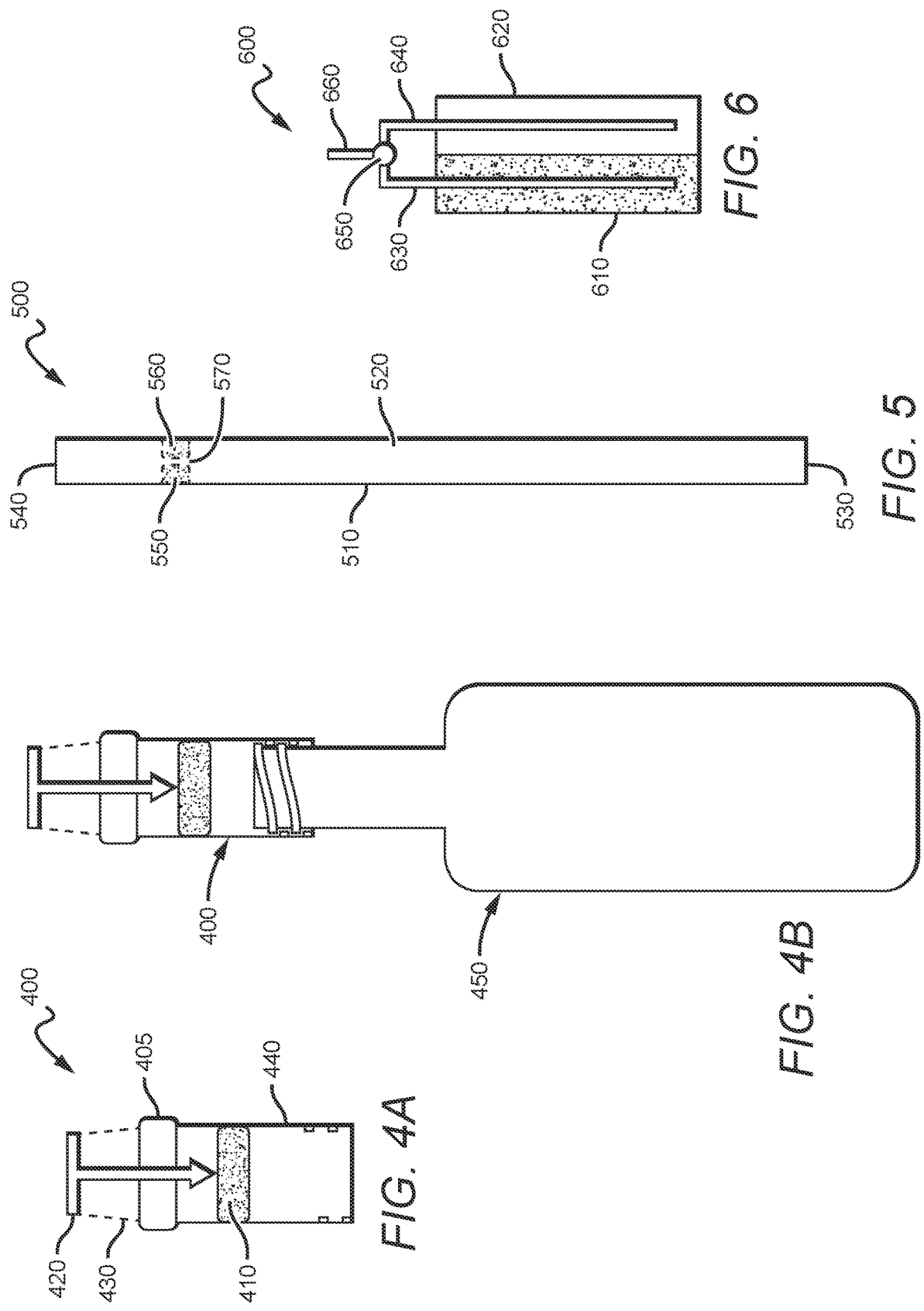

METHOD FOR PROVIDING A BEVERAGE ADDITIVE

This application is a divisional application of U.S. patent application Ser. No. 16/036,789 filed on Jul. 16, 2018. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is beverage additives, more specifically beverage additives that include bacteria.

BACKGROUND

The following description includes information that may be useful in understanding the present invention. It is not an admission that any of the information provided herein is prior art or relevant to the presently claimed invention, or that any publication specifically or implicitly referenced is prior art.

Oral disease, such as dental caries, is a significant health care issue, compounded by the prevalence of sugar and other carbohydrate-based sweeteners in the modern diet. In addition, stained teeth are cosmetically unappealing.

Tooth surfaces are absorbent and can become stained or discolored by the use of tobacco products, eating or drinking certain foods and beverages (e.g., coffee, tea and red wine), the buildup of dental plaque, the process of aging, diseases, trauma, medications, congenital conditions, and other environmental effects. Teeth are comprised of an inner dentin layer, an outer enamel layer and an acquired pellicle. The acquired pellicle is a proteinaceous layer derived from saliva that forms on the surface of tooth enamel.

Regular brushing with a dentifrice and regular dental care are effective in treating and reducing the prevalence of oral disease and improving their appearance. Extrinsic and intrinsic staining of the teeth can occur. Extrinsic staining is staining of the acquired pellicle that can occur when compounds such as tannins and polyphenolic compounds come in contact with teeth during eating, drinking or smoking. These compounds then become trapped in and tightly bound to the proteinaceous layer on the surface of the teeth. Extrinsic staining can be removed by mechanical methods of tooth cleaning, such as brushing or flossing and by chemical cleaning methods. Even with regular brushing and flossing, rapid or slow accumulation can develop into noticeable intrinsic tooth discoloration. Intrinsic staining can be caused by staining compounds that penetrate the enamel layer and the dentin layer or can arise from sources within the tooth. Intrinsic staining is difficult to remove and cannot typically be removed by mechanical methods of tooth cleaning, but high chemical concentrations and/or prolonged chemical cleaning methods can be used to remove some or all of this type of staining.

White, unstained teeth are considered cosmetically desirable. Teeth can be whitened by, for example, mechanical cleaning methods, veneers that are placed over the teeth, and chemical bleaching.

While tooth whitening products are known in the art, these products are traditionally used by those seeking the cosmetic benefit of whiter teeth. However, there is a different population of consumers who desire whiter teeth and/or more oral benefits including cleaner teeth, healthier gums, and decreased oral malodor. Therefore, there is a desire to provide oral hygiene products that can deliver oral care benefits in addition to tooth whitening. Furthermore, oral hygiene time is typically limited and so there is a desire to deliver these oral care benefits quickly and conveniently as part of a daily oral hygiene regimen. As a result less intrusive treatment modalities have been pursued. Among these are the use of bacteria that can inhabit the oral cavity but do not cause oral disease. Such bacteria can, for example, release compounds that improve or prevent an oral disease or condition (such as peroxide), or can colonize the oral cavity and displace disease-causing bacteria. Effective delivery of such bacteria in an acceptable manner, however, remains challenging.

Various means for introducing beneficial bacteria into humans have been proposed, however to date these have been directed towards directing relatively robust bacteria to the human gut (i.e. stomach, small intestine, and/or large intestine). Such approaches emphasize rapid passage through the mouth and upper portions of the digestive tract in order to preserve viability, and as such do not provide sufficiently slow release for colonization of the mouth. In addition, labile bacteria are not suitable for such applications. Australian Patent Application Publication No. 2008317000, to Moore, describes treatment of obesity by administration of a *Bacteroides* bacteria, with such administration intended to introduce the bacteria to the gut of the person being treated. All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. Although use of a liquid carrier is mentioned it is not clear how this would be accomplished. United States Patent Application Publication No. 2007/0098847, to Teissier, describes the use of dehydrated and granulated "lactic bacteria" that has been coated with a solid vegetable fat in foods, which provides protection from moisture and release in the gut. While the application mentions introduction of such coated granules into liquids it is not clear how such granules would be subsequently consumed, as they would presumably separate out from the solution.

European Patent Application No. 1020123, to Vesely and Milano, described beverages that include a mixture of three different "lactic bacteria" species, which are prepared by adding a lyophilized bacterial preparation to the beverage immediately prior to consumption. The lyophilized bacteria can be provided in a "plug" for the container holding the beverage, which is opened and the contents mixed with the beverage prior to consumption. Similarly, U.S. Pat. No. 5,895,648, to Vesely et al, describes the use of a pair of containers, one of which contains a consumable liquid, cream or paste and the other of which contains a lyophilized mixture of bacteria, wherein the container that holds the lyophilized bacteria is opened and mixed with the consumable material at the moment of consumption. U.S. Pat. No. 5,170,888, to Goncalves, describes a container with two compartments that contain components to be mixed prior to use and are separated by a membrane. The container includes a rotating blade that advances along a screw thread when turned in order to pierce the membrane and allow mixing of the components. U.S. Pat. No. 6,105,760, to Mollstam and Casas, describe a similar device, and additionally described using a detached drinking straw to pierce such a membrane. EP Patent Application No. 2341008, to Biogaia et al, describes a device for mixing a moisture sensitive component with a liquid component immediately prior to use. The moisture sensitive component is sealed within a portion of a cap behind a frangible barrier. The cap also includes a piston device that locks into two positions; movement between the two positions forces the end of the piston through the frangible barrier to release the moisture sensitive component into the liquid. It should be appreciated, however, that such methods and devices are intended for the delivery of probiotic mixtures to the gut. As such they dispense the entire volume of dehydrated or lyophilized bacteria into the liquid volume, where they are consumed as a dilute and uniform suspension.

Thus, there is still a need for a convenient and acceptable way to deliver bacteria to the oral cavity of a person.

SUMMARY OF THE INVENTION

The inventive subject matter provides apparatus, systems and methods in which a stabilized probiotic bacteria composition is introduced into the oral cavity of an individual at concentrations and for a period of time that permits at least transient colonization of surfaces of the oral cavity, for example the surfaces of the teeth and/or gums. The probiotic bacterial composition is provided as a component of a probiotic beverage. As defined herein, the term beverage is inclusive of a consumable liquid, wet foam, gel, or other fluid substance. In a preferred embodiment the probiotic bacterial composition is provided in a stabilized form (for example, an anhydrous form) that is mixed with an aqueous component by a user at or immediately prior to the time of consumption to form the probiotic beverage.

One embodiment of the inventive concept is beverage additive that includes an isolated, non-pathogenic, hydrogen peroxide bacterial species or strain and a genetically modified LDH-deficient bacterial strain and a metabolizable carbon source (e.g. a carbohydrate), where the bacterial formulation is or includes a stabilized bacteria preparation (for example, a lyophilized bacterial population, bacteria in an edible oil suspension, etc.). Such a stabilized bacteria preparation can also include a stabilizing agent. Suitable isolated, non-pathogenic, hydrogen peroxide-producing bacterial species or strains include *Lactobacillus, Bifidobacteria, viridans Streptococcus, Leuconostoc, Pediococcus*, and *Lactococcus*. Suitable genetically modified LDH-deficient bacterial strains include a genetically modified strain of *Streptococcus mutans*.

Another embodiment of the inventive concept is beverage additive device that includes a beverage additive, which in turn includes an isolated, non-pathogenic, hydrogen peroxide bacterial species or strain and an LDH-deficient bacterial strain. The isolated, non-pathogenic, hydrogen peroxide bacterial species or strain and the LDH-deficient bacterial strain are provided as a stabilized bacteria preparation. The beverage additive device also includes a moisture resistant barrier that encloses the beverage additive, along with a disrupting mechanism positioned to circumvent the moisture resistant barrier (for example, by displacing, rupturing, or piercing the barrier) and place the stabilized probiotic bacterial preparation in contact with a consumable aqueous solution. In some embodiments the moisture resistant barrier includes a packet that encloses the beverage additive, where the packet is essentially impermeable to water. In some embodiments the moisture resistant barrier is a submergible body, and can be positioned within an aperture or a lumen or passage of the beverage container. Such a submergible body can include a wall, an interior volume that encloses the bacterial formulation, and a through hole that traverses the wall. In some embodiments the beverage additive device is incorporated into a beverage container. In other embodiments the beverage additive device is configured to reversibly couple to a beverage container.

Another embodiment of the inventive concept is a beverage additive device that includes a body with an interior flow channel, a lower aperture, and an upper aperture. The beverage additive device also includes an isolated, non-pathogenic, hydrogen peroxide bacterial species or strain and an LDH-deficient bacterial strain, where the isolated, non-pathogenic, hydrogen peroxide bacterial species or strain and the LDH-deficient bacterial strain are provided as a stabilized bacteria preparation. The stabilized bacteria preparation is attached or adhered to at least a portion of an inner wall of the flow channel of the beverage additive device. In some embodiments a porous membrane (which can includes one or more pores) is positioned between the stabilized bacteria preparation and an interior space of the flow channel. In such embodiments at least a portion of the one or more pores are occupied by a water soluble compound. Such a beverage additive device can be configured to fit through an opening in a beverage container, for example as a drinking straw. In some embodiments the beverage additive device is provided in packaging that includes a dessicant.

Another embodiment of the inventive concept is a fluid dispensing device that includes a first reservoir containing an isolated, non-pathogenic, hydrogen peroxide bacterial species or strain and an LDH-deficient bacterial strain, where the isolated, non-pathogenic, hydrogen peroxide bacterial species or strain and the LDH-deficient bacterial strain are provided as a stabilized bacteria preparation (for example, as a suspension in an edible oil). The fluid dispensing device also includes a second fluid reservoir the contains a fluid vehicle. First and second flow channels are in fluid communication with the first and second fluid reservoirs, respectively, and with a valve. In some embodiments the first and second flow channels are separate channels that couple to the valve at distinct and different Positions. In other embodiments the first and second flow channels are segments of a common flow channel that couples to the valve. A dispensing channel (which can include mixing features) is in fluid communication with the valve, which in turn provides fluid communication between the first and second reservoirs when in the open position. Either or both of the first and second fluid reservoirs can be pressurized, for example by containing liquids that incorporate a dissolved gas. The fluid contents of either or both of the first and second fluid reservoirs can also include additional components that aid in providing the desired form or function of the final fluid product produced by the device, such as a surfactant and/or a pharmaceutical compound.

Another embodiment of the inventive concept is a method of introducing a probiotic formulation to an oral cavity, by providing a beverage additive device that incorporates a probiotic beverage additive, a moisture resistant barrier that encloses the beverage additive, and a disrupting mechanism that is placed or positioned to circumvent the moisture resistant barrier and place the stabilized probiotic bacterial preparation in contact with an aqueous solution. The disruption mechanism is activated to generate a consumable beverage, gel, or wet foam, and the consumable beverage or wet foam in contact with the oral cavity for a period of time sufficient for the bacteria of the probiotic beverage additive to adsorb or otherwise adhere to a surface of the oral cavity. The probiotic beverage additive includes an isolated, non-pathogenic, hydrogen peroxide bacterial species or strain and an LDH-deficient bacterial strain in the form of a stabilized bacteria preparation. In some embodiments the method includes a step of reversibly coupling the beverage additive device to a beverage container enclosing the consumable aqueous solution. In some embodiments the disrupting mechanism includes a valve, and the method further includes a step of opening the valve.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIGS. 4A and 4B depict a device of the inventive concept that couples to a beverage container reversibly. FIG. 4A shows a cross section of a example of such a device, with a housing that includes threads complementary to threads of a beverage container. FIG. 4B depicts a device as shown in FIG. 4A engaged with a beverage container having a threaded opening.

FIG. 5 depicts an embodiments of the inventive concept in which a probiotic bacterial preparation is placed within a flow channel of a device used for drinking liquids.

FIG. 6 depicts and embodiment of the inventive concept that utilizes materials stored in separate reservoirs that are mixed upon use to generate a consumable beverage, wet foam, or gel.

DETAILED DESCRIPTION

Figure 3:
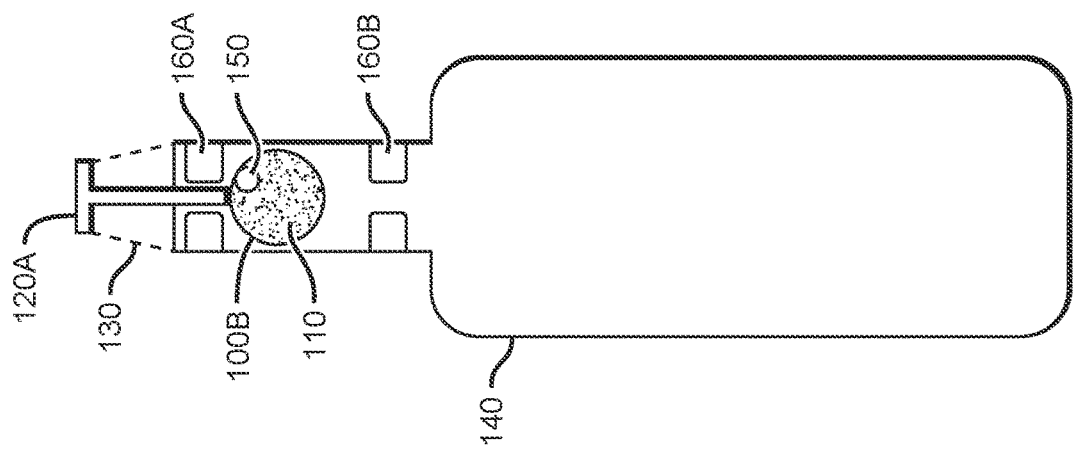
FIG. 3 shows another alternative beverage container of the inventive concept.

Embodiments of the inventive concept provide methods and devices that dispense preparations of bacteria that can occupy or colonize the oral cavity of a user on consumption of a beverage. These bacteria can be selected displace or suppress the growth of bacteria responsible for various oral conditions, such as dental caries, xerostomia, and/or halitosis. Such bacterial preparations can be relatively labile, being intolerant of the human digestive tract and becoming non-viable rapidly on liquid suspension if not provided with a suitable surface for colonization. In some embodiments a stabilized (for example, by drying, lyophilization, and/or the use of a preservative compound) preparation of orally-colonizing bacteria is provided in a sealed container, envelope, capsule, or similar enclosure that is pierced or otherwise accessed immediately prior to beverage consumption. In some embodiments such access results in dispensing of the entire or nearly (e.g. greater than 70%) volume of the stabilized probiotic bacterial suspension into a beverage to be consumed. In other embodiments a significant fraction (e.g. greater than about 30% of the stabilized probiotic bacterial preparation) is retained in the accessed enclosure following the initial piercing action, and is released from the enclosure gradually on beverage consumption. In such an embodiment the orally colonizing bacteria retained in the accessed enclosure can show extended viability relative to those in free suspension in the bulk beverage. Similarly, in such an embodiment orally colonizing bacteria can be released at relatively high concentration from the accessed enclosure on taking the beverage into the mouth, the high concentration of bacteria improving the efficiency of colonization of oral surfaces (e.g. teeth, mucosa, etc.) of a user. One should appreciate that embodiments of the inventive concept provide a simple and attractive way to introduce beneficial bacteria into the oral cavity.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

The instant invention provides methods and compositions for the introduction of beneficial probiotic bacteria to the oral cavity, which can be useful in maintenance of oral health (for example, tooth whitening). A composition of the invention includes one or more isolated, non-pathogenic, hydrogen peroxide-producing species or strains of bacteria, and optionally, LDH-deficient *mutans Streptococcus*. Certain bacteria can produce hydrogen peroxide at a level that can whiten teeth, and potentially effect a desired change in appearance and/or structure of a tooth surface. Examples of appearance and structural changes include, but are not necessarily limited to, whitening, stain bleaching, stain removal, plaque removal, and tartar removal. Furthermore, colonization of the oral cavity by beneficial bacteria can provide additional oral care benefits such as reducing the incidence of dental caries, reducing the incidence of periodontitis, reducing the incidence of oral bacterial infections, reducing the incidence of yeast or fungal overgrowth, reducing the incidence and/or severity of halitosis, reducing the incidence or severity of xerostomia, promotion of wound healing, or a combination of such effects.

The invention provides compositions and methods for improving oral health and/or whitening tooth surfaces using a composition that includes a mixture of probiotic bacteria that includes one or more non-pathogenic, hydrogen peroxide-producing *viridans Streptococci* species or strains, and/or one or more non-pathogenic, hydrogen peroxide-producing *Lactobacillus* species or strains and/or one or more non-pathogenic, hydrogen peroxide-producing *Bifidobacteria* species or strains and/or one or more non-pathogenic, hydrogen peroxide producing *Lactococcus* species or strains and/or one or more non-pathogenic, hydrogen peroxide producing *Pediococcus* species or strains and/or one or more non-pathogenic, hydrogen peroxide producing *Leuconostoc* species or strains.

In one embodiment of the invention the bacterial strains can be generally recognized as safe (GRAS), and can transiently attach, adhere, and/or adsorb to a tooth surface by virtue of electrostatic interactions, van der Waals interactions, or protein or polysaccharide adhesins on the bacterial surface that recognize and interact with molecules present on the tooth surface.

Examples of *viridans Streptococci* species include, but are not limited to *S. sanguis, S. parasanguis, S. gordonii, S. oralis, S. uberis, S. mitis, S. rattus, S. salivariaus, S. vestibularis, S. angionosus, S. constellatus, S. intermedius, S. mutans, S. sobrinus, S. milleri, S. cricetus,* and *S. mitior*. Examples of *Lactobacillus* species include, but are not limited to, *L. acidophilus, L. jensenii, L. catenaforme, L. leichrnanni, L. plantarum, L. johnsonii, L. gasseri, L. delbrueckii, L. casei, L. brevis, L. salivarius, L. gasseri, L. sobrius, L. rhamnosus, L. reuteri, L. fermentum, L. paracasei, L. dextranicurn,* and *L. helveticus*. Examples of *Bifidobacteria* species include, but are not limited to *B. angulatum, B. animalis, B. asteroides, B. bifidum, B. boum, B. breve, B. catenulatum, B. choerinum, B. coryneforme, B. cuniculi, B. dentium, B. gallicum, B. gallinarum, B indicum, B. longum, B. magnum, B. merycicum, B. minimum, B. pseudocatenulatum, B. pseudolongum, B. psychraerophilum, B. pullorum, B. ruminantium, B. saeculare, B. scardovii, B. simiae, B. subtile, B. thermacidophilum, B. thermophilum,* and *B. urinali*. Examples of other non-pathogenic bacteria that can produce hydrogen peroxide include, without limitation, *Pediococcus* species, such as *P. acidilactici, Leuconostoc* species, such as *L. mesenteroides, Lactococcus* species such as *L. lactis*.

The quantity of hydrogen peroxide produced by bacteria can be experimentally determined. See e.g. Hillman and Shivers, *Arch. Oral. Biol.*, 33:395-401 (1988). The culture liquor of cells grown in the presence of oxygen is incubated with 40 µg/ml horseradish peroxidase and 0.4 µmol/ml o-dianisidine. After 2 minutes, the reaction is stopped by the addition of 0.02 ml of 5N HCL. The optical density of the sample is measured at 410 nm and the hydrogen peroxide concentration of the sample is calculated from a standard curve prepared using authentic hydrogen peroxide and an extinction coefficient at 230 nm of $81M^{-1}cm^{-1}$. In one embodiment of the invention the bacteria can produce at least about 0.5, 1, 2, 5 mM or more of $H_2O_2$ or any range or value between about 0.1 and about 5 mM.

In one embodiment of the invention a composition of the invention includes one or more isolated *Streptococcus oralis* strains and/or one or more *S. uberis* strains. Compositions of the invention can optionally comprise one or more isolated strains or species of *mutans Streptococcus* that are LDH-deficient. Colonization of the oral cavity with such a combination of non-pathogenic, hydrogen peroxide-producing bacteria and/or *mutans Streptococcus* provides a significant practical advantage in that the colonization of the oral cavity with such a combination can reduce the incidence of dental caries, reduce the incidence of periodontitis, reduce the incidence of oral bacterial infections, reduce healing time for oral wounds, reduce the incidence of *Candida* and/or fungal overgrowth, reduce the incidence and/or severity of xerostomia, and can reduce discoloration of tooth enamel.

*Streptococcus oralis* (previously known as *S. sanguis* Type II) and *S. uberis* are important components in maintaining the normal, healthy balance of microorganisms that comprise the periodontal flora. See Socransky et al., *Oral Microbiol. Immunol.* 3:1-7 (1988); Hillman and Shivers, *Arch. Oral. Biol.*, 33:395-401 (1988); Hillman et al., *Arch. Oral. Biol.*, 30:791-795 (1985). *S. oralis* can also be found in dental plaque and has been demonstrated to correlate with periodontal health, in particular by interfering with the colonization by periodontal pathogens such as *Aggregatibacter actinomycetemcomitans, Porphyromonas gingivalis, PeptoStreptococcus micros,* and *Campylobacter rectus*. Compositions of the invention can comprise one or more isolated strains of *S. oralis*, for example, ATCC 35037, ATCC 55229, ATCC 700233, ATCC 700234 and ATCC 9811. Other strains of *S. oralis* include KJ3 and KJ3sm. KJ3sm is a naturally occurring genetic variant of KJ3 that is resistant to 1 mg/ml streptomycin. The streptomycin resistance is advantageous because it provides a marker for easy isolation of the bacteria. Additionally, streptomycin resistant strains are slightly attenuated and do not survive as long in an oral cavity as wild-type strains. This property is useful where the goal is to non-persistently colonize the oral cavity of an animal with the probiotic bacteria.

*S. uberis* can also be found in dental plaque and has been demonstrated to correlate with periodontal health, in particular by interfering with the colonization by periodontal pathogens such as *Tannerella forsythensis, P. micros, C. rectus,* and *Prevotella melaninogenica*. Compositions of the invention can comprise one or more isolated strains of *S. uberis*, for example, ATCC 13386, ATCC 13387, ATCC 19435, ATCC 27958, ATCC 35648, ATCC 700407, ATCC 9927, strain KJ2 or strain KJ2sm. KJ2sm is a naturally occurring genetic variant of KJ2 that is resistant to 1 mg/ml streptomycin and provides the same advantages as for streptomycin-resistant strains of *S. oralis*. One or more isolated strains of *S. oralis* or one or more isolated strains of *S. uberis*, or both, can be used in compositions and methods of the invention.

Compositions of the invention can include a mixture of probiotic bacteria that includes one or more isolated *mutans Streptococcus* bacteria species deficient in the production of lactic acid. These species include, for example, *S. rattus, S.*

*cricetus, S. mutans, S. sobrinus, S. downeii, S. macacae,* and *S. ferus.* A *mutans Streptococcus* of the invention does not substantially produce L(+) lactate dehydrogenase (LDH). Such a strain is termed an LDH-deficient strain. An LDH-deficient strain of *mutans Streptococcus* produces 75%, 80%, 90%, 95%, 98%, 99%, or 100% less lactic acid than wild-type strains of *mutans Streptococcus.* An LDH-deficient *mutans Streptococcus* strain can be a naturally occurring strain of *mutans Streptococcus* or a genetically modified strain of *mutans Streptococcus.* LDH-deficient *mutans Streptococcus* can compete with and/or displace pathogenic bacteria such as *S. mutans,* a principal etiological agent of dental caries, in the oral cavity. LDH-deficient *mutans Streptococcus* stains will compete with *S. mutans* for the same nutrients, colonization sites, etc. Therefore, colonization of the oral cavity with LDH-deficient *mutans Streptococcus* strains is associated with prevention and/or reduction of the incidence of dental caries. LDH-deficient strains of *mutans Streptococcus* are non-pathogenic, alter the microenvironment of the oral cavity to prevent colonization or outgrowth of pathogenic organisms, and/or displace pathogenic organisms from the oral cavity where the pathogen is part of the host's indigenous flora.

Examples of LDH-deficient *mutans Streptococcus* strains include, for example, *S. rattus* JH145 (ATCC 31377) (a spontaneous, naturally-occurring LDH-deficient mutant) and JH140 (ATCC 31341) (a chemically-modified LDH-deficient mutant). See e.g., Stanshenko & Hillman, Microflora of plaque in rats following infection with an LDH-deficient mutant of *Streptococcus rattus,* Caries Res. 23:375-377 (1989); Hillman, Lactate dehydrogenase mutants of *Streptococcus mutans*: Isolation and preliminary characterization. Infect. Immun. 21:206-212 (1978); see also Abhyankar et al., Serotype c *Streptococcus mutans* mutatable to lactate dehydrogenase deficiency. J. Dent. Res. 64:1267-71 (1985).

An LDH-deficient strain of *mutans Streptococcus* can be derived from a *mutans Streptococcus* strain using, for example, chemical or physical mutagenesis techniques. Strains that are mutagenized using these techniques are considered genetically modified strains. For example, a *mutans Streptococcus* strain can be subjected to mutagens such as nitrous acid, formic acid, sodium bisulphate, UV light, base analog mutagens, including for example, 5-bromo-deoxyuridine (5BU), alkylators such as ethyl methane sulfonate (EMS), methyl methane sulfonate (MMS), diethylsulfate (DES), and nitrosoguanidine (NTG, NG, MNNG). See e.g., In Vitro Mutagenesis Protocols, Braman, Ed., Humana Press, 2002.

Naturally-occurring, spontaneous LDH-deficient *mutans Streptococcus* strains can be prepared using methods disclosed in, for example, Hillman, Lactate dehydrogenase mutants of *Streptococcus mutans*: isolation and preliminary characterization. Infect. Immun. 21:206-212 (1978). Spontaneous LDH-deficient mutants occur at the rate of approximately $10^{-5}$ frequency. See Johnson et al., Cariogenic potential in vitro in man and in vivo in the rat of lactate dehydrogenase mutants of *Streptococcus mutans.* Arch. Oral Biol. 25:707-713 (1980).

Naturally-occurring, spontaneous LDH-deficient strains of *mutans Streptococcus* can be differentiated from LDH-producing strains of *mutans Streptococcus* by plating the bacteria on glucose tetrazolium medium. LDH-deficient *mutans Streptococcus* colonies will be bright red and relatively larger in size than colonies of the parent strain, which are white and relatively smaller in size on the glucose tetrazolium medium. Naturally-occurring, spontaneous LDH-deficient strains of *mutans Streptococcus* can be used in a composition of the invention.

An LDH-deficient strain of *S. rattus* has been isolated. Briefly, a culture of *S. rattus* BHT-2 was grown overnight to saturation in Todd Hewitt broth, and diluted samples were spread on glucose tetrazolium medium to give approximately 300 colonies per plate. Wild-type, acid producing colonies are white on this medium. LDH-deficient mutants are bright red. *S. rattus* JH145 was one red colony amid approximately 100,000 white colonies that were screened. *S. rattus* JH145 is therefore a naturally-occurring, LDH-deficient mutant.

LDH-deficient strains of *mutans Streptococcus,* such as LDH-deficient mutants of *S. rattus* BHT-2, produce less total titratable acid when incubated in the presence of glucose and other sugars or polyols, make substantially less lactic acid when incubated in the presence of glucose in the case of resting and growing cultures, adhere better to hydroxyapatite and accumulate more plaque when grown in the presence of sucrose. LDH activity can be assayed as described by Brown & Wittenberger (J. Bacteriol. 110:604, 1972).

Terminal pH can be determined by subculturing strains (1:100) in Todd-Hewitt broth containing 1% glucose. After 48 hours incubation in candle jars at 370 C, the absorbance at 580 nm and pH of the cultures can be determined. Lactic acid concentration of cultures can be determined by gas-liquid chromatography. See Salanitro & Muirhead, Quantitative method for the gas chromatographic analysis of short-chain monocarboxylic and dicarboxylic acids in fermentation media. Appl. Microbiol. 29:374-381 (1975); Hillman et al., Acetoin production by wild-type strains and a lactate dehydrogenase-deficient mutant of *Streptococcus mutans.* Infect. Immun. 55:1399-1402 (1987). Additionally, any genetic modification techniques known to those of skill in the art can be used to create an LDH-deficient *mutans Streptococcus* strain from an LDH-producing *mutans Streptococcus* parent strain. For example, an LDH gene or a portion of an LDH gene can be deleted or mutagenized, including, for example, insertional mutagenesis techniques. Other mutagenesis techniques include, for example, homologous recombination, recursive sequence recombination, oligonucleotide-directed mutagenesis, site-directed mutagenesis, error-prone PCR, phosphothioate-modified DNA mutagenesis, uracil-containing template mutagenesis, gapped duplex mutagenesis, point mismatch repair mutagenesis, repair-deficient host strain mutagenesis, radiogenic mutagenesis, deletion mutagenesis, restriction-selection mutagenesis, restriction-purification mutagenesis, site saturation mutagenesis, ensemble mutagenesis, recursive ensemble mutagenesis, and chimeric nucleic acid creation. Therefore, any genetic modification technique that disables an LDH gene can be used to produce an LDH-deficient *mutans Streptococcus* strain. In one embodiment of the invention, the LDH-deficient strains, whether naturally-occurring or genetically-modified mutants, have a reversion frequency less than $10^{-7}$ and produce less than about 10% of the parental level of lactate dehydrogenase activity.

The use of two or more different species of bacteria can provide an advantage over using a single species. This is because different species of bacteria colonize different surfaces or portions of teeth. Therefore, the use of more than one species of bacteria can be used to "blanket" all or most surfaces of the teeth, whereas the use of only one species of bacteria may result in certain surfaces or portions of the teeth being uncolonized. Therefore, all surfaces of the teeth are exposed to whitening action.

Compositions of the invention can further comprise one or more carbon sources that are metabolizable by the one or more isolated, non-pathogenic, hydrogen peroxide-producing bacterial species or strains or the one or more lactate dehydrogenase deficient *mutans Streptococcus* species or strains or both types of species or strains. Carbons sources include, but are not limited to, for example, glucose, sorbitol, mannitol, fructose, galactose, maltose, sucrose, xylose, lactose, glycerol or combinations thereof.

The compositions of the invention can comprise a pharmaceutically acceptable or nutritionally acceptable carrier. The carrier is physiologically compatible with the oral cavity of the subject to which it is administered. Carriers can be comprised of solid-based, dry materials for formulation into tablet, capsule, lozenge, or powdered form. A carrier can also be comprised of liquid or gel-based materials for formulations into liquid, gel, and chewing gum forms. Suitable liquid or gel-based carriers include but are not limited to: water, physiological salt solutions, urea, alcohols and derivatives, and glycols (e.g., ethylene glycol or propylene glycol). The composition of the carrier can be varied so long as it does not interfere significantly with the therapeutic activity of the bacterial strains of the invention.

A composition can be formulated to be suitable for oral administration in a variety of ways, for example in a semi-solid, liquid (including, e.g., a viscous liquid, a paste, a gel, or a solution), a dried mass, a dentifrice, a mouth wash, an oral rinse, a liquid suspension, a topical agent, a paste, a gel, a solid food, an oral rinse, and the like. Other formulations will be readily apparent to one skilled in the art. A composition of the invention can include a nutrient supplement component and can include any of a variety of nutritional agents, as are well known, including vitamins, minerals, essential and non-essential amino acids, carbohydrates, lipids, foodstuffs, dietary supplements, and the like.

Compositions of the invention can also include natural or synthetic flavorings and food-quality coloring agents, all of which are compatible with maintaining viability of the bacterial species or strains of the invention.

A composition of the invention can include one or more gelling agents. The concentration of the gelling agent may be greater than about 2, 4, 6, 8, 10, 15, 20, 30, 40, 50, 60, 70, 80 or less than about 80, 70, 60, 50, 40, 30, or 20 percent by weight of the composition.

Suitable gelling agents and adhesion agents useful in the present invention include, for example, silicone, polyethylene oxide, polyvinyl alcohol, poly alkyl vinyl ether-maleic acid copolymer (PVM/MA copolymer) such as, Gantrez AN 119, AN 139, and S-97, polyvinyl alcohol, polyacrylic acid, Poloxamer 407 (Pluronic), polyvinyl pyrrolidone-vinyl acetate copolymer (PVP/VA copolymer), such as Luviskol VA, and Plasdone S PVP/VA, polyvinyl pyrrolidone (PVP, e.g., K-15 to K-120), Polyquaterium-11 (Gafquat 755N), Polyquaterium-39 (Merquat plus 3330), carbomer or carboxypolymethylene (Carbopol), hydroxy propyl methyl cellulose, hydroxy ethyl cellulose, hydroxy propyl cellulose, corn starch, carboxymethyl cellulose, gelatin and alginate salt such as sodium alginate, natural gums such as gum karaya, xanthan gum, Guar gum, gum arabic, gum tragacanth, and mixtures thereof.

A humectant or plasticizer can be present in compositions of the invention. Humectants or plasticizers include, for example, glycerin, glycerol, sorbitol, polyethylene glycol, propylene glycol, and other edible polyhydric alcohols. The humectants or plasticizers can be present between at about 1% to about 99%, about 10% to about 95%, or at between about 50% and about 80% (or any range between 1% and 99%) by weight of a composition.

Bacteria of the invention can be prepared in, for example, a fermenter. The bacteria can be harvested from the fermenter and can be, for example, concentrated. Bacteria of the invention can be prepared for use by, for example, dehydration or spray drying. Spray drying generally comprises spraying a suspension of bacteria in a vessel and under a steam of hot air. Bacteria can also be prepared for use by microencapsulation (see e.g., U.S. Pat. No. 6,251,478), freeze-drying, or by coating with a protective substance such as, for example, lipid material such as triacylglycerols, waxes, organic esters, soybean oil, cottonseed oil, palm kernel oil, and esters of long-chain fatty acids and alcohols.

Methods of Whitening Teeth

The invention provides methods for delivering a composition that provides one or more oral care benefits, including tooth whitening, to the surfaces of the oral cavity comprising applying a composition of the invention to the teeth and/or adjacent soft tissue of a subject.

The bacterial species or strains can be present in a composition of the invention in a therapeutically effective amount. Therapeutically effective means effective to alleviate, reduce, prevent and/or ameliorate one or more symptoms of dental caries, periodontitis, bacterial infections or diseases, oral wounds, *Candida* or fungal overgrowth, halitosis, or xerostomia-induced dental caries or periodontal disease or to alleviate, reduce, prevent, or ameliorate stains or discoloration on the teeth either permanently or temporarily. Therapeutically effective also means effective to promote wound healing in an oral cavity.

A therapeutically effective amount is an amount of a composition of the invention at high enough levels to provide effective colonization of the oral cavity, but low enough to avoid serious side effects (at a reasonable benefit/risk ratio). The therapeutically effective amount of a composition of the invention may vary with the condition of an individual's oral cavity, the age and physical condition of the individual being treated, the severity of any pathologies within the oral cavity, the duration of treatment, the nature of any concurrent therapy, the specific form of the source employed, and the particular vehicle from which the composition is applied.

The compositions of the invention can be applied in a therapeutically effective amount to the mucosal tissue of the oral cavity, to the gingival tissue of the oral cavity, to the surface of the teeth and/or any combination thereof for the treatment and/or prevention of stained and/or discolored teeth. A composition of the invention may be swallowed or may rinsed around the oral cavity and spit out.

The bacterial strains of the invention can form at least a part of the transient or indigenous flora of an oral cavity and exhibit additional beneficial prophylactic and/or therapeutic effects in the cavity. Such exposure and/or colonization of the oral cavity can have a beneficial effect on dental caries, periodontitis (including, for example, early-onset periodontitis, localized and generalized juvenile periodontitis, and rapidly progressive and adult periodontitis), oral bacterial infections and diseases, oral wounds, *Candida* or fungal overgrowth, halitosis, or xerostomia-induced dental caries, wound healing, or a combination thereof.

Compositions can be administered to an oral cavity of a subject such as an animal, including a mammal, for example, a human, a non-human primate, a dog, a cat, a rat, a mouse, a horse, a goat, or a rabbit.

One embodiment of the invention provides a method of non-persistently colonizing an oral cavity of a subject with therapeutically-effective bacteria comprising administering to the oral cavity of a subject a composition of the invention. In one embodiment of the invention the administered bacterial strains do not permanently colonize the oral cavity, rather the strains are present in the oral cavity for about 1 day, about 1 week, about 2 weeks, about 3 weeks, about 1 month, about 3 months or about 12 months after administration of the bacteria.

Compositions of the invention can be administered at a dose of about $1\times10^3$, $1\times10^5$, $1\times10^7$, $1\times10^9$, or $1\times10^{11}$ CFU (or any range or value between about $1\times10^3$ and about $1\times10^{11}$) of viable bacteria. A dose of a composition of the invention can be administered at three times a day, twice a day, once a day, every other day, two times a week, weekly, biweekly, or monthly. One, two, or more doses of a composition of the invention can be administered per day for about 1 week, about 2 weeks, about 1 month, about 2 months, about 3 months, about a year or more.

Compositions of the invention can be used daily as part of an oral care regimen. Using compositions of the invention as part of a daily oral care regimen allows a user to achieve and sustain a variety of desired oral care benefits, including but not limited to white, tartar-free teeth.

A composition of the invention can be applied to the teeth and/or soft tissue for between about 1 minute and about 8 hours. In some embodiments, the composition can be applied for greater than about 1, 2, 3, 4, 5, 6, 7, 8, 9, 10, 15, 20, 30, 40, 50, 60, 90, 120, 150, 180, 210, 240, 270, 300, 330, 360, 390, 420, 450, 480 minute(s) (or any range or value between about 1 and about 480 minute(s)) and/or less than 480, 450, 420, 390, 360, 330, 300, 270, 240, 210, 180, 150, 120, 90, 60, 50, 40, 30, 20, 15, 10, 9, 8, 7, 6, 5, 4, 3, 2 or 1 minute(s) (or any range or value between about 480 and about 1 minute(s)) and any combination thereof, wherein the bacterial species or strains have a concentration between about 0.01% and about 50%, or about 0.1% to about 25%, or about 1.0% to about 10% or any ranges or values in between 0.01% and 50% by weight of the composition. Such a regimen could be advantageously used once a day for greater than about one month, two months, four months, six months, twelve months, eighteen months, two years, five years, eight years, ten years and/or less than about fifteen years, ten years, eight years, five years, two years, 18 months, 12 months, six months, four months, two months, one month and any combination thereof. In another embodiment such a regimen could be advantageously used once or twice a day for greater than about one month and less than about 5 years.

A kit of the invention can contain a one month, two month, three month, four month, five month, six month, or 12 month supply of a composition of the invention. A composition of the invention can be packaged and, in turn, a plurality of the packaged compositions can be provided in a storage container or outer package or carton.

Figure 2:
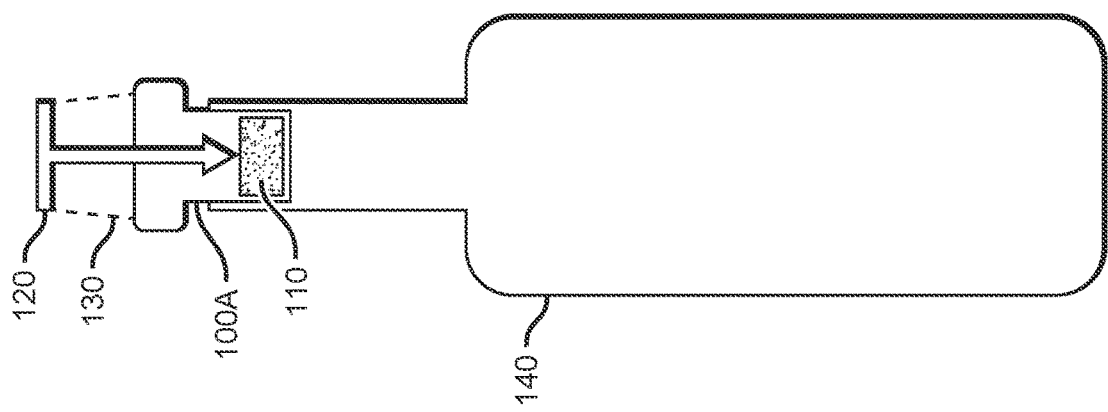
FIG. 2 shows an alternative beverage container of the inventive concept.

Embodiments of the inventive concept include devices and compositions that provide controlled release of beneficial probiotic bacteria as described above (which can be relatively labile), which in turn releases the bacteria into the oral cavity during consumption of a beverage in numbers and over a period of time sufficient to encourage colonization of oral surfaces. Examples of such devices and compositions are shown in FIGS. 1 to 3.

Figure 1:
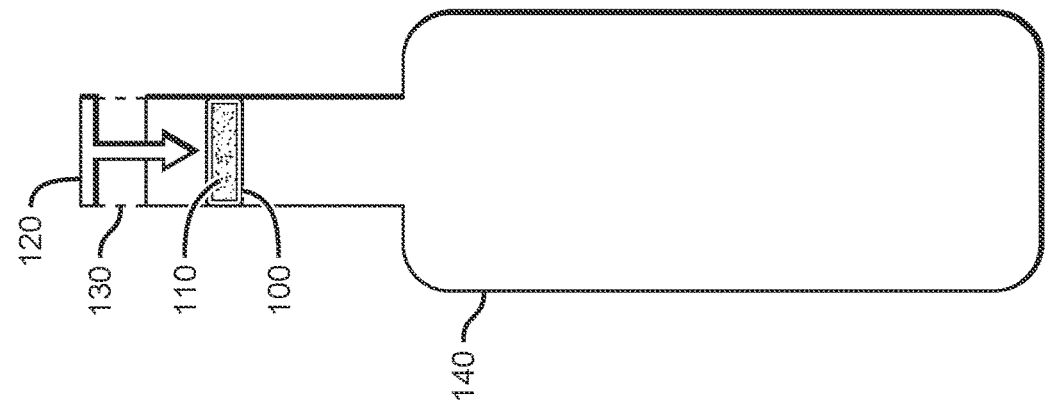
FIG. 1 shows a beverage container of the inventive concept.

FIG. 1 shows an embodiment of the inventive concept in which a stabilized probiotic bacterial preparation (as described above) is incorporated into a delivery system that instills the bacterial preparation into a liquid that is consumed by a user. In such an embodiment a dried or otherwise stabilized probiotic bacterial preparation 110 is provided in a moisture resistant or water-proof enclosure 100. Suitable moisture resistant or water-proof enclosures include a foil and/or plastic lined pouch, packet, or sachet. In some embodiments the moisture resistant or water proof enclosure can incorporate a portion of the walls of an associated beverage container 140, for example by providing moisture resistant or water-proof barriers that are fixed to an inner wall of the beverage container and that enclose a dried or otherwise stabilized probiotic bacterial preparation within an intervening space. A puncturing tool 120 is provided that can be used by a user to puncture or rupture the moisture resistant or water-proof enclosure 100 in order to release the probiotic bacterial preparation 110 into a beverage. The puncturing tool 120 can be attached to the beverage container 140, for example by one or more tool support(s) 130 that align the puncturing tool with the moisture resistant or water-proof enclosure. The tool support 130 can be perforated or constructed of a relatively weak or thin material in order to provide sufficient mechanical strength to support the puncturing tool 120 during manufacturing and shipping, but to be fragile enough to allow a user to crush or deform the tool support upon use. In some embodiments the puncturing tool 120 can be secured using a string, line, tether, or similarly flexible attachment that allows a user to grasp the puncturing tool and move it into position to puncture or rupture the moisture resistant or water-proof enclosure.

In some embodiments the enclosure 100 can be retained in a liquid flow path of the beverage container, and the puncturing tool 120 dimensioned to provide one or more through-holes that provide retention of about 30% or more of the volume of probiotic bacterial preparation within the enclosure 100 following puncture or rupture. Such a through-hole can be from 100 μm to 5 mm in diameter, and the number of through-holes provided on use of the puncturing tool 120 can range from 1 to 100 or more. Towards that end the puncturing tool 120 can be provided with one or more shafts with a maximum diameter of 100 μm to 5 mm. In such embodiments the retained bacteria can be released into the oral cavity of the user on swallowing a portion of the beverage. In other embodiments rupture of the enclosure 100 can release essentially all of the bacteria (e.g. about 70% or more) into a beverage held within the enclosure to form a relatively homogenous bacterial suspension.

In order to use such a delivery system a user can utilize the puncturing tool 120 to pierce or otherwise rupture the moisture resistant or water-proof enclosure and release the stabilized probiotic bacterial preparation. On release at least a portion of the stabilized probiotic bacterial preparation can fall into a beverage contained in the lower portion of the beverage container 140. In some embodiments at least a portion (for example, at least 10%, 20%, 30%, 40%, 50%, 60%, 70%, 80%, 90%, 95%, 99%, or more than about 99%) of the stabilized probiotic bacterial preparation is retained in the punctured enclosure following puncturing, and is released into the oral cavity of a user on flow of the beverage through the remains of the enclosure on consumption.

In other embodiments the stabilized probiotic bacterial preparation can be provided in a filter or similarly porous envelope or container that is positioned to avoid puncture or rupture by the puncturing tool when in use. Such a filter or similarly porous envelope can retain all or some of the bacterial mass within the fluid flow path as the beverage is consumed. In some embodiments such a filter or similarly porous envelope can be displaced into the interior of the beverage container following rupture of the enclosure by the puncturing tool, and subsequently release bacteria into the beverage over a period of time (for example, 30 seconds to 30 minutes). Such an embodiment advantageously retains labile bacteria that may be sensitive to the beverage's composition over time in a relatively protected environment, and provide a continuous supply of active bacteria to the oral cavity on consumption of the beverage.

In another embodiment of the inventive concept the moisture resistant or water-proof enclosure can be configured as a closure 100A of the beverage container 140, as shown in FIG. 2. In such an embodiment the closure 100A can include a friction surface for gripping an internal wall of the beverage container 140, for example in a neck portion of the beverage container, as is typical for a bottle closure or stopper. The closure 100A can enclose the dried or otherwise stabilized probiotic bacterial preparation 110, and can include one or more a piercable or frangible wall(s). These can support and/or surround the bacterial preparation 110. A puncturing tool 120 is provided that can be positioned to puncture or rupture the piercable or frangible wall of the closure 100A. As shown, the puncturing tool 120 can be incorporated into or traverse a portion of the closure 100A, and supported by one or more tool support(s) as described above. Alternatively, the puncturing tool can be provided on a tether, line, or other flexible support that is attached to the beverage container 140 and permits a user to maneuver the puncturing tool into position.

In some embodiments the enclosure 100A can include a through-hole through which the beverage can be consumed, and can be retained or replaced in a liquid flow path of the beverage container, and the puncturing tool 120 dimensioned to provide one or more through-holes that provide retention of about 30% or more of the volume of bacterial preparation within the enclosure 100A following puncture or rupture. In such embodiments the retained bacteria can be released into the oral cavity of the user on swallowing a portion of the beverage. In other embodiments rupture of the enclosure 100A can release essentially all of the bacteria (e.g. about 70% or more) into a beverage held within the enclosure to form a relatively homogenous bacterial suspension. In such an embodiment the enclosure 100A can be removed and/or discarded following puncture or rupture.

In order to use such a delivery system a user can utilize the puncturing tool 120 to pierce or otherwise rupture the moisture resistant or water-proof enclosure 100A and release the stabilized probiotic bacterial preparation. On release at least a portion of the stabilized probiotic bacterial preparation can fall into a beverage contained in the lower portion of the beverage container 140. In some embodiments at least a portion of the stabilized probiotic bacterial preparation is retained in the punctured enclosure, and can optionally be released into the beverage by manipulation of the beverage container 140 by the user (for example, by shaking, rocking, and/or inverting the container.

In another embodiment of the inventive concept, shown in FIG. 3, the moisture resistant or water-proof enclosure is provided as a capsule 100B that encloses a dried or otherwise stabilized probiotic bacterial preparation 110. The capsule 100B can, for example, lie within a neck, lumen, or other extension of an associated beverage container 140. In some embodiments the capsule is affixed to an interior wall of the beverage container 140, and acts prevent release of its contents prior to consumption. In some of such embodiments the capsule 100B is affixed in a temporary manner, and can be dislodged as described below, to permit consumption of a contained beverage. Once dislodged such a capsule 100B can be retained in this portion of the beverage container by one or more stops. As shown, an upper stop 160A and a lower stop 160B can be provided to retain the capsule 100B with the beverage container and prevent premature release of the bacterial preparation 110, respectively. Such a stop can, for example, be configured as a continuous or discontinuous ring or collar, as one or more rod(s), bump(s) or similar projections into the neck or lumen, or as a net or mesh. Such a stop can be formed from the material of the beverage container, or can be provided as an added appliance that is coupled to the beverage container. In some embodiments the lower stop 160B can be pliant, such that the capsule 100B inserts into the body of the beverage container 140 on use, and can be retained therein.

As shown, a dispensing tool 120A is provided. In some embodiments the dispensing tool 120 can include a terminus, point, projection, or other cutting or puncturing portion that can create one or more opening(s) in the capsule 100B when wielded by a user. This permits the beverage to enter the punctured s capsule and release at least a portion of the bacterial preparation into the beverage on consumption. In other embodiments the dispensing tool 120A is configured to simply dislodge the capsule, thereby permitting flow of the beverage around the dislodged capsule. In such an embodiment the capsule can include one or more aperture(s) 150, which permit release of at least a portion of the bacterial preparation into the beverage on consumption. If an aperture is present in the capsule the beverage container 140 can be provided with a moisture resistant or water-proof seal that encloses the open end of the neck of the beverage container prior to use. In such embodiments the aperture 150 can be oriented such that it is not exposed to the beverage prior to dislodging of the capsule 100B.

In some embodiments the enclosure 100B can be retained in a liquid flow path of the beverage container, and the puncturing tool 120 dimensioned to provide one or more through-holes that provide retention of about 30% or more of the volume of bacterial preparation within the enclosure 100B following puncture or rupture. In such embodiments the retained bacteria can be released into the oral cavity of the user on swallowing a portion of the beverage. In other embodiments rupture of the enclosure 100B can release essentially all of the bacteria (e.g., about 70% or more) into a beverage held within the enclosure to form a relatively homogenous bacterial suspension.

Another embodiment of the inventive concept is a dispensing device that can be attached to a pre-existing commercial beverage container, for example bottle water, a soft drink, etc. An example of such an embodiment is shown in FIG. 4A. The device 400 includes an enclosure 410 that provides a water/moisture barrier that surrounds a stabilized probiotic bacterial preparation as described above. The enclosure can be placed within a housing 440 that interfaces with the beverage container. Such a housing can, for example, be dimensioned to slip over the neck of such a container, insert into the neck or opening of such a beverage container, and/or include threads that engage complementary threads of such a beverage container. As shown in FIG. 4B, in use the device 400 is reversibly coupled to a beverage container 450 via such a housing. The housing 440 can be coupled to a guide 405, through which passes a dispensing tool 420. Such a dispensing tool can include a projection, blade, point, or similar device that is positioned to rupture or otherwise disrupt the water/moisture barrier when it is depressed. In some embodiments the dispensing tool can be held in a pre-dispense position by a temporary support 430. Such a temporary support can be removed by a user, or crushed or similarly deformed by a user through the application of downwards pressure on the dispensing tool 420 in order to dispense the stabilized probiotic composition into a beverage held within the beverage container.

Another embodiment of the inventive concept is a device that can be inserted into a liquid beverage, and through which a user applies suction to consume the beverage through a channel or lumen of the device. An example of such a device is shown in FIG. 5. As shown, the device 500 can be configured as an elongated tube or straw, with a wall 510, a channel or lumen 520 through which liquid passes when in use, a lower aperture 530 that is submerged in a beverage while in use, and an upper aperture 540 that is placed in or at the entrance of the oral cavity when in use. The device includes an insert that contains stabilized probiotic bacteria 550 as described above. The stabilized probiotic bacteria are adhered to the wall of the channel or lumen 520, and in some embodiments can be at least partially covered by a porous wall or membrane 560, which is in turn affixed to the wall of the lumen 520. The pores of the porous wall or membrane 560 can be occupied by a water-soluble filler (such as a water soluble polymer) that prevents moisture from reaching the stabilized probiotic bacteria prior to use. Alternatively, in embodiments where no porous wall or membrane is present or where the pores are left unoccupied the device 500 supplied in a water resistant container or envelope (for example, an envelope or container that includes a dessicant). If present, a porous wall or membrane can include a vent feature 570 that permits some flow of fluid from the lower aperture 530 to the upper aperture 540 when suction is applied to the upper aperture. In use the lower aperture 530 is inserted into a beverage to be consumed and suction applied by the user to the upper aperture 540. Movement of the liquid beverage through the lumen dislodges the stabilized probiotic material for transport to the oral cavity. In embodiments that include a porous wall or membrane in which the pores have been filled such liquid would initially dissolve the water-soluble material from the pores and subsequently release the stabilized probiotic bacteria through the pores and into the oral cavity.

Another embodiment of the inventive concept is a device that provides a consumable and flowable suspension, emulsion, gel, and/or wet foam by mixing the contents of a fluid reservoir that includes stabilized probiotic bacteria and a second fluid reservoir that includes a vehicle. One or both of such reservoirs can be pressurized (for example, with nitrogen, nitrous oxide, air, etc.) to provide a motive force for moving the contents of these reservoirs through fluid flow channels, and for combining the contents of the reservoirs at or near a dispensing nozzle. An example of such an embodiment is shown in FIG. 6. As shown, such a device 600 includes a first reservoir 610, which includes stabilized probiotic bacteria. Such stabilized bacteria are provided in a liquid or other flowable media, for example an edible oil. The device 600 also includes a second reservoir 620, which includes a flowable vehicle, for example an aqueous solution. Such an aqueous solution can include compounds that aid in forming the suspension, emulsion, gel, and/or wet foam, for example surfactants, wet foam stabilizers, thickeners, etc. Either or both of the reservoirs 610, 620 can include additional compounds that are useful in combination with the probiotic bacteria, including carbohydrates, flavoring agents, coloring agents, minerals that support or reinforce tooth enamel, and/or pharmaceutical compounds.

As shown in FIG. 6, the reservoirs 610, 620 each have an associated flow channel (630 and 640, respectively) through which reservoir contents flow when the device is activated. The driving force for such flow can be provided by a pressurized or dissolved gas, which can be either included in a reservoir or placed in fluid communication with it. It some embodiments both reservoirs are pressurized and dispensing of reservoir contents occurs through individual flow channels associated with each reservoir. In other embodiments only one of the reservoirs is pressurized, and flow is provided by placing both reservoirs along a common flow channel. Dispensing of the contents of the reservoirs can be activated by opening a valve 650, which opens communication between the flow channels 630, 640 and a dispensing channel 660. The dispensing channel 660 can include mixing features to improve blending of the contents of the reservoirs, for example projections into the interior dispensing channel, configuration of some or all of the dispensing channel as a tortuous path, and variations in the cross section of the dispensing channel.

Mixing of reservoir contents in the dispensing channel 660 provides a consumable and flowable material that incorporates the probiotic bacteria. The nature of the consumable and flowable material is at least partially dependent on the contents of the reservoirs 610, 620. For example, blending of an edible oil suspension of probiotic bacteria in reservoir 610 with an aqueous solution in reservoir 620 can provide an oil-in-water emulsion. Inclusion of a surfactant in one or both reservoirs can provide a micellar suspension. Inclusion of a dissolved gas in one or both of the reservoirs can provide a wet foam. Inclusion of a gel-forming polymer (such as an alginate) in one reservoir and an activating component (such as a calcium salt) in the remaining reservoir can provide a gel.

One embodiment of the invention provides a method of non-persistently colonizing an oral cavity of a subject with a mixture of probiotic bacteria that includes bacteria which do not produce (or produce at reduced levels relative to wild type bacteria) acids that can degrade tooth enamel. In a typical method a composition of the invention is administered to the oral cavity of a subject, for example as described above. In one embodiment of the invention the administered bacterial strains do not permanently colonize the oral cavity, rather the strains are present in the oral cavity for about 1 day, about 1 week, about 2 weeks, about 3 weeks, about 1 month, about 3 months or about 12 months after administration of the bacteria. Without wishing to be bound by theory, the Inventor believes that such colonization can at least transiently reduce the population of potentially harmful wild type bacteria with the oral cavity.

Compositions of the invention can be administered at a dose of about $1\times10^3$, $1\times10^5$, $1\times10^7$, $1\times10^9$, or $1\times10^{11}$ CFU (or any range or value between about $1\times10^3$ and about $1\times10^{11}$) of viable bacteria. A dose of a composition of the invention can be administered at three times a day, twice a day, once a day, every other day, two times a week, weekly, biweekly, or monthly. One, two, or more doses of a composition of the invention can be administered per day for about 1 week, about 2 weeks, about 1 month, about 2 months, about 3 months, about a year or more.

Compositions of the invention can be used as part of an oral care regimen. Using compositions of the invention as part of a daily oral care regimen allows a user to achieve and sustain a variety of desired oral care benefits, including but not limited to white, tartar-free teeth.

A kit of the invention can contain a one week, two week, one month, two month, three month, four month, five month, six month, or 12 month supply of a composition of the invention, and also can include instructions for use. The composition within the kit can be individually packaged as distinct dose units. Alternatively, a plurality of the packaged compositions can be provided in a storage container or outer package or carton. In some embodiments a kit of the inventive concept can include features or components that improve stability of the product, for example a dessicant.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C ... and N, the text should be interpreted as requiring only one element from the group, not A plus N, or B plus N, etc.

What is claimed is:

1. A method of introducing a probiotic bacterial formulation to an oral cavity of an individual, comprising;
    providing a beverage container, comprising:
        a flow path providing flow of fluid contents of the beverage container out from the beverage container;
        a probiotic bacterial beverage additive composition comprising an isolated, non-pathogenic, hydrogen peroxide bacterial species or strain and an LDH-deficient bacterial strain, wherein the isolated, non-pathogenic, hydrogen peroxide bacterial species or strain and the LDH-deficient bacterial strain are provided as a stabilized bacteria preparation;
        a passage encompassing a submergible body comprising a moisture resistant barrier that encloses the beverage additive, wherein the passage comprises an upper stop and a lower stop positioned to retain the submergible body within the flow path, wherein the submergible body is movable between the upper and lower stops; and
        a dispensing mechanism positioned to circumvent the moisture resistant barrier and place the stabilized bacteria preparation in contact with fluid contents of the beverage container on passage of fluid contents of the beverage container through the flow path;
    activating the dispensing mechanism; and
    dispensing a mixture of the stabilized bacteria preparation and fluid contents of the beverage container to the oral cavity.

2. The method of claim 1, wherein the moisture resistant barrier comprises a packet enclosing the beverage additive, and wherein the packet is essentially impermeable to water.

3. The method of claim 1, wherein the dispensing mechanism is reversibly coupled to the beverage container.

4. The method of claim 1, wherein the dispensing mechanism comprises a puncturing device positioned to contact the submergible body on use, and wherein activation comprises puncturing the submersible body with the puncturing device.

5. The method of claim 4, wherein the puncturing device is coupled to a plunger, and wherein activation comprises depressing the plunger.

* * * * *